United States Patent [19]

Berg et al.

[11] Patent Number: 4,606,346
[45] Date of Patent: Aug. 19, 1986

[54] INTRANASAL DEVICE

[76] Inventors: Olle Berg, Elfviksvägen 66, S-181 90 Lidingö ; Lars Lejdeborn, Västergöksvägen 70, S-162 24 Vällingby, both of Sweden

[21] Appl. No.: 688,483
[22] Filed: Jan. 3, 1985

[30] Foreign Application Priority Data

Jan. 11, 1984 [SE] Sweden .............................. 8400125

[51] Int. Cl.⁴ ............................................ A61M 29/00
[52] U.S. Cl. .................................. 128/342; 128/344; 128/87 R; 128/89 R
[58] Field of Search ..................... 128/342, 344, 87 R, 128/89 R; 604/99; 137/224

[56] References Cited

U.S. PATENT DOCUMENTS

| 1,235,095 | 7/1917 | Beck ..................... 128/344 |
| 2,179,964 | 11/1939 | Stevens ................. 128/344 |
| 2,265,387 | 12/1941 | McMillin ............... 128/344 |
| 2,493,326 | 1/1950 | Trinder ................. 128/342 |
| 2,638,093 | 5/1953 | Kulick .................. 128/344 |
| 2,691,985 | 10/1954 | Newsom ................ 128/342 |
| 3,049,125 | 8/1962 | Kriwkowitsch ..... 128/342 |
| 3,516,407 | 6/1970 | Ruggero ............... 128/342 |
| 3,935,859 | 2/1976 | Doyle ................... 128/89 R |
| 4,044,793 | 8/1977 | Krueger et al. ........ 604/99 |
| 4,338,941 | 7/1982 | Payton ................. 128/342 |

FOREIGN PATENT DOCUMENTS 2435183 4/1975 Fed. Rep. of Germany ...... 128/344

Primary Examiner—Robert Peshock
Assistant Examiner—Cary E. Stone
Attorney, Agent, or Firm—Pollock, Vande Sande and Priddy

[57] ABSTRACT

An intranasal device to be used in combination with septum operations consists of a breathing channel and an inflatable balloon positioned in side by side relation to one another on one side of a thin plate which is shaped to conform to the interior anatomy of the nasal cavity. The balloon is connected to a pressure balancing device for controlling the pressure in the balloon, and valve means are provided for setting a maximum allowable pressure in the balloon.

6 Claims, 1 Drawing Figure

U.S. Patent      Aug. 19, 1986      4,606,346
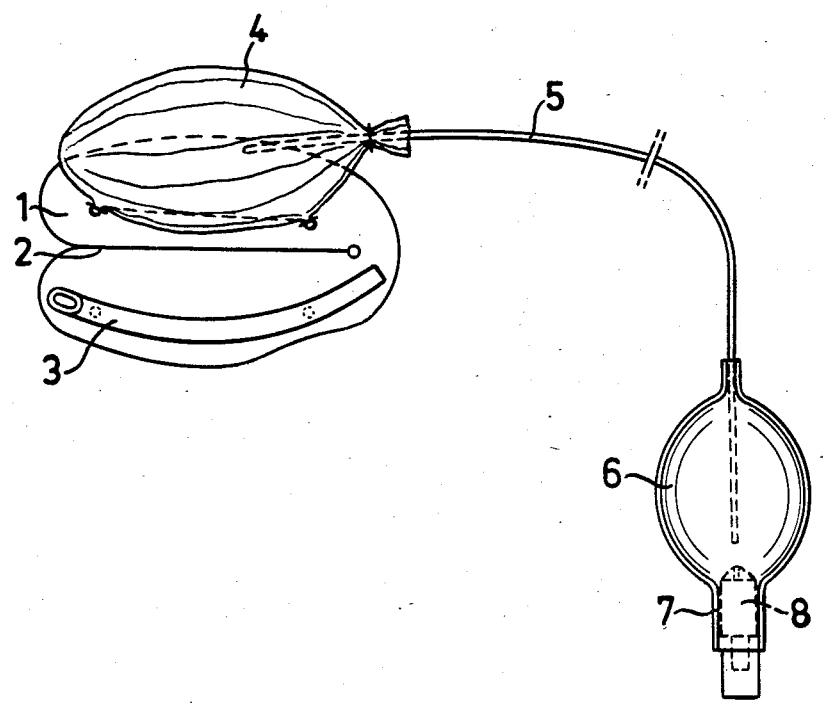

INTRANASAL DEVICE

The present invention relates to an intranasal device to be inserted into a nasal cavity in connection with nasal operations such as septum operations and other plastic surgical procedures.

For a number of years prior to the present invention, thin plates of plastic material, so called splints, have been used in order to post operatively support the nasal septum. The plates are positioned on each side of the septum and are fixed with sutures, whereupon the nasal cavities are packed with tampons or foam plastic. The plates must thereafter remain in the nasal cavities at least one week, but the tampons or foam plastic are removed after a few days since otherwise the discomfort for the patient would be too great and the infection risk would increase considerably.

The foregoing method has obvious disadvantages. The patient, during the first days cannot breathe through the nose or pressure compensate when swallowing, and furthermore the tampon/foam plastic is a reservoir for coagulates and secretions with accompanying risk for infections which can jeopardize the operation result. Moreover, the removal of the tampon/foam plastic can involve considerable discomfort for the patient.

The object of the present invention is to eliminate the above mentioned disadvantages, discomforts and infection risks. By the present invention normal breathing is ensured to the patient in combination with the fact that an even and well-defined pressure, which is guaranteed not to exceed a maximum allowed pressure and during the whole treatment time is controllable, is obtained and maintained in the nose. Moreover, is possibly to easily effect a successive decrease of the pressure and also possible to effect a simple and painless removal of the nasal device from the nose. Also the insertion of the device into the nose is accomplished with minimum discomfort for the patient and the insertion can be carried out by principally all doctors without the demand for specialist training, or even by otherwise educated personnel.

An embodiment of a nasal device according to the invention is described more in detail with reference to the accompanying drawing.

The nasal device illustrated in the drawing consists of a thin plastic plate or splint 1 provided, as shown, with a slit 2. This slit is, however, not necessary but can be omitted. The plate is shaped to conform to the anatomy of the nasal cavity, particularly to the cavity bottom where the greatest stability is required, or can be easily cut to so conform. A breathing channel 3 made of plastic material and a balloon 4 (shown in flat state) made of thin plastic material are fixed to the plate 1 on the same side of the plate and, as shown in the embodiment, on each side of the slit 2. As shown in the drawing, the breathing channel 3 is curved, and is located adjacent to and substantially follows the curved contour of a longitudinal edge of plate 1. The breathing channel 3 can be a tube closed in cross section as shown, or it can be partly open, for instance downwardly. One end of a plastic hose 5 is air-tightedly inserted into the balloon 4 and the other end of the hose projects into a pressure balancing device or balloon 6. A back valve 8 is inserted onto a neck 7 of the device 6. The neck 7 can be connected to an air pressure source (not shown) and a pressure gauge (not shown) can also be provided.

When carrying out nasal septum operations or other plastic surgical incisions in a nose, plates 1 are reversedly positioned on each side of the nasal septum with the surfaces thereof that are not provided with the breathing tube 3 and balloon 4 abutting the nasal septum for the support thereof. The breathing tube 3 ensures the patient normal breathing, and after being inflated the balloon 4 provides an even and well-defined counter pressure. The back valve 8 is set on a maximum pressure not exceeding the capillary bed pressure (about 25 mm Hg), thereby guaranteeing that no pressure injuries are obtained on the nasal menosa. When the counter pressure no longer is required, most often after two or three days post operative, the plastic balloon 4 can be evacuated by means of an ordinary syringe. The balloon 4 can then, if desired, be removed by cutting of the attachment of the balloon at the plate. Due to the fact that the plastic balloon does not cause crust or the like (as distinguised from tampons or foam plastic as previously used) the counter pressure can, if so is desired, be maintained without risk for infections.

We claim:

1. An intranasal device for insertion into a nasal cavity following a septum operation, comprising a thin plate which is shaped to conform to the interior anatomy of the nasal cavity, a breathing channel attached to one side of said plate, an inflatable balloon of thin-walled material attached to said one side of said plate in laterally spaced side-by-side relation to said breathing channel, the side of said plate opposite to said one side being adapted to abut the nasal septum to provide support for the septum when said plate and the breathing channel and balloon attached thereto are inserted into the nasal cavity, and inflation means attached to said balloon for inflating said balloon, said inflation means including means for maintaining a controlled pressure in said balloon.

2. The intranasal device of claim 1 wherein said breathing channel is of curved configuration and extends adjacent to and substantially follows the contour of a curved longitudinal edge of said plate.

3. The intranasal device of claim 1 or 2 wherein said balloon is removably attached to said plate.

4. The intranasal device of claim 1 wherein said inflation means includes control means for setting a maximum allowable pressure in said balloon.

5. The intranasal device of claim 4 wherein said inflation means includes an air supply hose one end of which is connected to said balloon, said control means comprising a valve connected to said hose.

6. The intranasal device of claim 5 wherein the other end of said hose is connected to one end of a pressure balancing device, said valve being connected to the other end of said pressure balancing device.

* * * * *